United States Patent [19]

Senuma et al.

[11] Patent Number: 4,879,118
[45] Date of Patent: Nov. 7, 1989

[54] GLYCYRRHETINIC ACID-CONTAINING PLASTERS

[75] Inventors: Makoto Senuma, Tokyo; Shigeru Kondoh, Saitama; Tadamasa Kawase, Saitama; Yoshihiko Nakagawa, Saitama, all of Japan

[73] Assignee: Yamanouchi Pharmaceutical Co., Ltd., Tokyo, Japan

[21] Appl. No.: 168,587

[22] Filed: Mar. 3, 1988

Related U.S. Application Data

[63] Continuation of Ser. No. 705,549, Feb. 26, 1985, abandoned.

[30] Foreign Application Priority Data

Mar. 7, 1984 [JP] Japan .................................. 59-41994

[51] Int. Cl.$^4$ ....................... A61F 13/02; A61L 15/06; A61K 31/19
[52] U.S. Cl. ........................................ 424/448; 424/81; 514/33; 514/572
[58] Field of Search ................... 424/448; 514/33, 572

[56] References Cited

U.S. PATENT DOCUMENTS

| | | | |
|---|---|---|---|
| 4,307,717 | 12/1981 | Hymes et al. ........................ | 128/156 |
| 4,455,146 | 6/1984 | Noda et al. .......................... | 604/897 |
| 4,490,322 | 12/1984 | Zierenberg ........................... | 264/205 |

OTHER PUBLICATIONS

Chemical Abstracts, 83:136887r, (1975).
Chemical Abstracts, 89:152655t, (1978).

*Primary Examiner*—Leonard Schenkman
*Attorney, Agent, or Firm*—Burgess, Ryan & Wayne

[57] ABSTRACT

An antipruritic plaster prepared by spreading a medicament-containing adhesive mass on a backing, said medicament-containing adhesive mass being obtained by dissolving glycyrrhetinic acids in at least one solvent selected from benzyl alcohol, phenethyl alcohol, diphenhydramine, chlorpheniramine, N-methyl-2-pyrrolidone, crotamiton, and lauric acid diethanolamide and uniformly mixing the solution with a plaster base composed of a rubber compound adhesive plaster base, a tackifying agent, and a softener as the necessary components of a plaster base composed of an acrylic resin as the necessary component.

6 Claims, No Drawings ed to 4,879,118

GLYCYRRHETINIC ACID-CONTAINING PLASTERS

This application is a continuation of application Ser. No. 705,549, filed 2/26/85 now abandoned.

FIELD OF THE INVENTION

This invention relates to an antipruritic plaster containing glycyrrhetinic acids as the indispensable medical component. More particularly, the invention relates to an antipruritic plaster prepared by dissolving a glycyrrhetinic acid in at least one solvent selected from benzyl alcohol, phenethyl alcohol, diphenhydramine, chlorpheniramine, N-methyl-2-pyrrolidone, crotamiton, and lauric acid diethanolamide and compounding the solution with a plaster base.

BACKGROUND OF THE INVENTION

Glycyrrhetinic acid is the hydrolyzed product of glycyrrhizin (glycyrrhizic acid) which is an extract component of Glycyrrhizae Radix, possesses an antiphlogistic activity and an antipruritic activity, frequently used as therapeutic agents for eczema, dermatitis neurotica, and pruritus cutanea.

Glycyrrhetinic acid itself is easily soluble in pyridine and somewhat soluble in ethanol and chloroform but is almost insoluble in fats and oils, hydrocarbons, and water, which makes the preparation thereof difficult.

Now, in the treatment for pruritus cutanea such as a skin disease and insect bite, it is necessary to select a form of preparation suitable to treat the cause of the itching, various skin symptoms, etc. However, in solution, the solvent is evaporated off by the body heat to deposit crystals, whereby the sufficient medical effect cannot be obtained and also a sufficient durability of the medical effect cannot be expected. On the other hand, in ointments, etc., the deposition of crystals of medicament is unavoidable in the case that the medical component has poor compatibility with the base, and hence the medical effect and the duration of effect thereof cannot be obtained. An ointment causes a defect that the ointment stains clothes by the stickiness of the ointment itself. A plaster may be considered as the form of preparation having no such defects but such a product has not yet been known as to antipruritic agents.

Hitherto, it is known that glycyrrhetinic acid is soluble in crotamiton and fatty acid dialkylamides, such as capric acid N,N-dimethylamide, etc., (Japanese Patent Publication Nos. 25,405/'67 and 25,406/'67 but as the preparations of glycyrrhetinic acid, only a solution of glycyrrhetinic acid dissolved in a volatile solvent such as ethanol, etc., as a solubilizer, an ointment mainly composed of the acid and polyethylene glycol, and a hydrophilic ointment mainly composed of the acid and a carboxyvinyl polymer are known at present (see, for example, Japanese Patent Publication Nos. 25,405/'67 and 25,406/'67; Japanese Patent Publication (OPI) No. 47,520/'74, the term "OPI" indicates an unexamined published patent application open to public inspection).

Also, various forms of preparations are known containing glycyrrhetinic acid esters or the salts thereof having an improved water solubility or oil solubility, (Japanese Patent Publication (OPI) Nos. 149,222/'82 and 27,815/'84) but the form of plaster has not yet been known.

On the other hand, in the field of plasters, a percutaneous administration of various medicaments, in particular, steroid hormones, nonsteroidal antiflammatory agents, antibacterials, antitumor agents, etc., has hitherto been attempted. For example, U.S. Pat. No. 4,307,717 and European Patent No. 72,251 describe antipruritic agents such as benzoin, calamine, camphor, menthol, phenol, sulfur, etc., in the descriptions on various medicaments and suggest that these antipruritic agents can be used in the form of a flexible liquidabsorbent or an adhesive bandage for antipruritic purpose but the techniques disclosed therein cannot be applied to water-insoluble glycyrrhetinic acid.

Also, Japanese Patent Publication (OPI) Nos. 15,861/'83; 105,915/'83 and 36,608/'84 describe that glyctrrhetinic acid and materials similar to glycyrrhetinic acid can be widely used as medicaments with specific bases for medicines for external application but there are no descriptions of practical preparations and the techniques described in them cannot be applied as they are to glycyrrhetinic acid which is insoluble in water and scarecely soluble in fats and oils.

At present, plasters containing glycyrrhenitic acids for antipruritics use are not known.

SUMMARY OF THE INVENTION

Thus, as the result of various investigations on the compatibility of glycyrrhetinic acids with various bases or other medicaments for developing antipruritic plasters containing glycyrrhenitic acids as the antipruritic medical component, the inventors have found that an ordinary ointment base such as a carboxyvinyl polymer is a poor base for a plaster and it is difficult to use the base for the preparation of plaster.

On the other hand, it has also been found that crotamiton which is known to have good compatibility with glycyrrhetinic acid but is not known as a plaster base and has never been used for plasters show good affinity for plasters using rubber compound adhesive plaster bases or acrylic resins.

Furthermore, it has been newly discovered that glycyrrhetinic acid is soluble in not only crotamiton but also in lauric acid diethanolamide, benzyl alcohol, phenethyl alcohol, diphenhydramine, chlorpheniramine, and N-methyl-2-pyrrolidone at a solubility higher than 10%, is soluble in diethylene glycol monoethyl ether at a solubility higher than 6%, and when the medicament is compounded with a plaster base, the medicament shows excellent compatibility and no deposition of cyrstals thereof is observed.

In particular, since benzyl alcohol, phenethyl alcohol, diphenhydramine, and chlorpheniramine not only increase the affinity between glycyrrhetinic acids and a plaster base but also has a local anesthetic action and an antipruritic action by itself, they have great merit as a compounding agent for antipruritic agents.

The present invetnion is based on new knowledge about the compatibility of three components, i.e. glycyrrhetinic acids, the solvent for dissolving glycyrrhetinic acids, and a plaster base and a plaster containing glycyrrhenitic acid has first been provided by the present invention.

In addition, it has also been found that aforesaid knowledge is common to glycyrrhizin and monoammonium glycyrrhizinate which show the same medical effect as that of glycyrrhetinic acid and are insoluble in water, fats and oils, and hydrocarbons and also dipotassium glycyrrhizinate which has the same medical effect as glycyrrhetinic acid and shows an improved solubility for water but is also inferior in the solubility for fats and oils and hydrocarbons.

Furthermore, there is a general recognition that the esters of glycyrrhetinic acid with higher fatty acids or higher aliphatic alcohols, such as glycyrrhetinic acid stearate and stearyl glycyrrhetinate may have somewhate improved solubility in fats and oils and hydrocarbons but show poor compatibility with a general plaster base. It has now been found that they have excellent compatibility with the specific bases of this invention and can be used for compounding the antipruritic plaster.

Accordingly, the term "glycyrrhetinic acids" as used in this application means not only glycyrrhetinic acid but also glycyrrhetinic acid esters, glycyrrhizin, and salts of glycyrrhrizin.

The object of this invention is, therefore, to provide an antipruritic plaster containing glycyrrhetinic acids as the necessary medical component.

That is, the invention is an antipruritic plaster comprising a backing having formed on one surface a pressure-sensitive layer containing (1) glycyrrhetinic acids, (2) at least one solvent for dissolving glycyrrhetinic acids selected from benzyl alcohol, phenethyl alcohol, diphenhydramine, chlorpheniramine, N-methyl-2-pyrrolidone, crotamiton, and lauric acid diethanolamide, (3) a base of either (a) or (b)

(a) at least one rubber compound adhesive plaster base selected from natural rubber, a styrene-butadiene copolymer elastomer, and a styrene-isoprene-styrene copolymer elastomer; at least one tackifying agent selected from a petroleum resin, rosin, hydrogenated rosin, and an ester gum; and at least one softener selected from polybutene, liquid paraffin, a higher fatty acid ester, a silicone oil, and a vegetable oil or (b) an acrylic resin as the necessary components of the medical effect component, the glycyrrhetinic acids solvent and the base, respectively.

DESCRIPTION OF THE PREFERRED EMBODIMENT

The antipruritic plaster of this invention comprises a self-adhesive plaster prepared by coating a backing such as flannel, a plastic film, a nonwoven fabric, etc., with an adhesive mass containing the aforesaid necessary components and includes various forms such as a sheet form, a film form, a tape form, a patch form, etc.

The antipruritic plaster of this invention may contain glycyrrhetinic acids as at least one antiflammatory and antipruritic component and does not exclude the inclusion of other antipruritic components and other medical effect component or components.

In particular, in the solvents for dissolving glycyrrhetinic acids, benzyl alcohol and phenethyl alcohol possess both a local anesthetic action and an antipruritic action and further the antihistamine agents such as diphenhydramine, chlorpheniramine, etc., and crotamiton possess an anti-pruritic action, and hence they can be used as suitable compounding agents for antipruritic agents.

Also, as the medicaments which may be compounded in the antipruritic plasters of this invention in addition to the aforesaid medical effective component, there are medicaments which do not dissolve glycyrrhetinic acid but do not destroy the compatibility with the plaster base and the glycyrrhetinic acids solvent even when the medicaments exist together with glycyrrhetinic acids. Examples of such a medicament are antihistamic agents salts of diphenhydramine (e.g., diphenhydramine hydrochloride), salts of chlorpheniramine (e.g., chlorpheniramine maleate), etc.; and antibacterials such as chlorhexidine gluconate, chlorhexidine dihydrochloride, dequalinium chloride, isopropylmethylphenol, benzalkonium chloride, benzethonium chloride, etc., and perfumes such as menthol, etc., which do not possess an antipruritic effect but are required or are desirably compounded for producing an antipruritic preparation.

The compounding amount of glycyrrhetinic acids for exhibiting an anti-inflamatory and antipruritic action as the effective amount is 0.5 to 10% by weight, preferably 1 to 4% by weight to the total amount of the medicament-containing adhesive mass in the case of the preparation of glycyrrhetinic acid alone containing no other medical effect component and/or the glycyrrhetinic acid solvent having an medicinal action and is 0.1 to 5% by weight, preferably 0.2 to 2% by weight of the total amount of the medicament-containing adhesive mass in the case of glycyrrhetinic acids containing other medical effect component and/or the glycyrrhetinic acids solvent having an medicinal action.

The amount of a glycyrrhetinic acids solvent is suitably 3 to 20 parts by weight per 1 part by weight of glycyrrhetinic acids (for dissolving), and the compounding amount of the solvent is 1 to 20% by weight, preferably 5 to 15% by weight to the total amount of the medicament-containing adhesive mass.

For producing the anti-pruritic plaster of this invention, glycyrrhetinic acids and, if necessary other medical effect component or components are dissolved in at least one solvent selected from benzyl alcohol, phenethyl alcohol, diphenhydramine, chlorpheniramine, N-methyl-2-pyrrolidone, crotamiton, and lauric acid diethanolamide and the solution is uniformly kneaded with a plaster base to form a medicament-containing adhesive mass.

The compounding amount of the whole medical effect components including a glycyrrhetinic acid and, other medical effect component or components is 1.5 to 30% by weight, particularly 3 to 20% by weight to the total amount of the adhesive mass.

As the plaster base, a base composed of a rubber compound adhesive plaster base, a tackifying agent, and a softener as the necessary components or a base composed of an acrylic resin as the necessary component is used.

As the rubber compound adhesive plaster base, there are natural rubber and synthetic rubbers such as a styrene-butadiene copolymer elastomer, a styreneisoprene-styrene copolymer elastomer, a silicone rubber, etc. As the tackifying agent or component, there are petroleum resins such as Quintons (registered trade name, aliphatic petroleum resin, made by Nihon Zeon K. K.), Alcone (registered trade name for an alicyclic petroleum resin, made by Arakawa Chemical Industries Co., Ltd.), etc., rosin, hydrogenated rosin, ester gum etc. Also, as the softener there are polybutene, liquid paraffin, a higher fatty acid ester such as isopropyl myristate, etc., a silicone oil, a vegetable oil, etc.

Also, if necessary, the following additives may be further added for producing the plasters of this invention. These additives include, for example, antioxidants such as butylated hydroxyanisole, guaiacol esters, butylated hydroxytoluene (BHT), nordihydroguaiaretic acid, etc., antiseptics such as thymol, etc., and diethylene glycol monoethyl ether as a solbilizer.

In addition, polybutene has tackiness by itself and hence functions as a tackifying component but can be used as a softener since polybutene has a function of softening a rubber component without need of the use of other softeners.

When an acrylic resin such as an acrylic acidacrylic acid ester series polymer, for example, Primal® N-580 and ASE60 (trade names for resins made by Acryl Chemical Co., Ltd.), etc., is used as the base, a suitable plaster of this invention can be produced without need of using the above-described rubber compound adhesive plaster base, tackifying agent, and softener. In this case, the acrylic resin is uniformly kneaded with the aforesaid medical effect component and, above described additives which are used in case of necessity to form a medicament-containing adhesive mass.

For producing a medicament-containing adhesive mass for a plaster, a solvent method, a hot melt method, an emulsion method, etc., is usually used and any of these methods can be used for producing the plaster of this invention.

In the case of use of a solvent method, a solution of glycyrrhetinic acids dissolved in the above-described specific solvent is dissolved (mixed) in an organic solvent and is mixed with a solution of the above-described base dissolved in an organic solvent and the mixture is uniformly kneaded. As the solvent for dissolving (mixing) the solution of the glycyrrhetinic acids and dissolving the base, an organic solvent which has a compatibility with the base and does not deposit crystals when the solvent is mixed with the solution of the selected glycyrrhetinic acids. Examples of such an organic solvent are toluene, carbon tetrachloride, chloroform, methylene chloride, etc.

Also, in the case of use of an emulsion method, a method of converting the whole medicament-containing adhesive mass into an emulsion is employed and the emulsion is prepared using a latex emulsion of a natural rubber or a synthetic rubber. The latex emulsion having a rubber content of about 40 to 80% is preferably used.

In the case of using the rubber compound adhesive plaster base, the tackifying agent, and the softener as the base, it is advantageous that the compounding amount of the rubber compound adhesive plaster base is about 15 to 60% by weight to the total amount of the medicament-containing adhesive mass, the compounding amount of the tackifying agent is about 15 to 60% by weight, and the amount of the softener is 5 to 30% by weight. Also, it is preferred that the total amount of the base is 75 to 98.5% by weight, particularly in the range of 80 to 97% by weight to the total amount of the medicament-containing adhesive mass.

Also, in the case of using acrylic resin as the base, the compounding amount thereof is 65 to 98.5% by weight, preferably in the range of 70 to 97% by weight to the total amount of the medicament-containing adhesive mass.

Further, in the case of using the base in the form of emulsion, it is proper that the compounding amount of the solid component is inside the range of above-described compounding ratio.

At the production of the medicament-containing adhesive mass, the addition order of adding the glycyrrhetinic acids, other medical effect components, the solvent for the medical effect components, and the base may be properly changed or heating or ultrasonic treatment may be desirably applied for accelerating the dissolution of the components in the solvent in any case of employing the above-described method.

The medicament-containing adhesive mass thus prepared is spread on a support or backing and a releasable film is applied on the adhesive mass layer or the medicament-containing adhesive mass is spread on a releasable film and a support or a backing is applied thereon. In addition, in the case of producing the plaster by applying the above-described solvent method or emulsion method, the solvent is evaporated off or water is removed by drying after spreading the adheisive mass, As the support or backing, a material usually used in the field of this art, such as plastic of film, flannel, an unwoven fabric, etc., can be used.

As the releasable film, a plastic film which has been subjected to a release treatment is usually used.

The plaster thus obtained is fabricated to a proper form on considering the disease to which the medicament is applied, the applying portion and the various symptoms. For example, for a dermatitis neurotica such as insect bite, etc., a patch which is handy to carry and easily applicable is most preferred.

The present invention first enables the provision of an antipruritic plaster containing glycyrrhetinic acids as the necessary medical effect component and according to this invention, an antipruritic plaster which can exhibit sufficient medical effect without depositing crystals of a glycyrrhetinic acids and other medical effect components and is excellent in durability is obtained. Thus, the industrial merits of this invention are great.

Furthermore, the antipruritic plaster of this invention is advantageous for making a concentrated treatment of a limited area and neither gives an unpleasant smell nor stains clothes by the stickiness as in ordinary oitments, etc.

Also, when the plaster is formed into a circular patch form, it is very handy to carry and very advantageous for the application in the case of insect bite, etc.

Then, the effect determing test for the antipruritic plaster of this invention and the result thereof are shown below.

(Test for comparing the effect of the product of this invention and a commercially available antipruritic agent for mosquito bite)

1. Test Procedure A (Determination test by medical doctor)

A tube for blood-sucking containing male imagos of *Aedes aegypti* in a blood-sucking period after the 2nd generation bred by hatching from the ovum is applied to the inner side of upper arms of 32 male and female healthy adults to perform sufficient blood-sucking. The test is applied simultaneously to three areas by one test. After performing blood-sucking for 10 minutes, leaving one area untreated, two bite areas are treated by applying thereto a commercially available anti-pruritic agent (Muhi®, made by Ikeda Mohando K. K., the main anti-pruritic agent: diphenhydramine, a solution for sticky coating) and a circular plaster (60–100 μm in thickness of the medicament-containing adhesive mass) prepared according to Example 8 of this invention, wherein the combination of the medicaments and the compounding ratio of the medicaments are changed to some extent in the scope of this invention (in addition, the medicaments of the plaster of this invention is a combination of glycyrrhetinic acids, diphenhydramine, crotamiton, and isopropylmethylphenol).

The effect determination to itching is recorded based on the subjective symptom of the testees with definite time intervals (0.5, 2, 4, 8, and 24 hours), the results are generally evaluated and compared with the effect by the commercially available antipruritic agent.

In addition, the effect determination for each symptom is evaluated in the following four stages according to the subjective symptom of the testees.

3—Very itchy (Itch is too severe and they cannot concentrate on their work)
2—Considerably itchy (Itch is strong and they cannot concentrate on their work although they can work)
1—A little itchy (Itch to an extent of not giving hindrance to work)
0—Not itchy Also, the general determination is performed by ranking from the effect determination for each symptom (in addition, a same effect is in a same rank) and the effect is compared by the percentage of the number of the testees in the 1st rank of the determination results.

Test Result:

| | |
|---|---|
| Product of this invention | 53.8% |
| Commercially available product | 20.5% |
| Untreated | 5.1% |
| No difference | 20.8% |

2. Test Procedure B (Panel test):

To 20 volunteers bitten by insect during the period from August, and the middle of September, was applied a sensitivity test for determining the effect of the product of this invention and for comparing the effect of the product of this invention and the effect of commercially available products. The answer was obtained from 16 volunteers.

The determination of the effects was evaluated in three stages of (1) quickly effective, (1) effective, and (3) not effective about itching and (1) suppressing well, (2) suppressing, and (3) not suppressing about swelling based on the subjective symptom of the testees.

The comparison to the commercially available products was made by the feelings of the testees on the comparison the effect of the product of this invention and the conventional commercially available product.

Test Result:

The results are shown by the percentage of the testees giving each evaluation:

| (1) | Using Effect of the Product of Invention: | |
|---|---|---|
| (a) | Itching | |
| | Quickly effective | 56.2% |
| | Effective | 43.8% |
| | Not effective | 0 |
| | No answer | 0 |
| (b) | Swelling | |
| | Suppressing well | 56.2% |
| | Suppressing | 12.5% |
| | Not suppressing | 6.3% |
| | No answer | 25.0% |
| (2) | Comparison with Commercially Available Product: | |

In addition, the commercially available products used and the percentage of the number of testees are as follows.

Muhi ® (same as Test Procedure A) 45%

Kinkan ® (trade name, made by Kinkando K. K., antipruritic effective component: aqueous ammonia, solution) 20%

Una Kowa ® (trade name, made by Kowa K. K., antipruritic effective component: diphenhydramine hydrochloride, solution) 10%

Makiron ® (trade name, made by Yamanouchi Pharmaceutical Co., Ltd., solution containing chlorpheniramine maleate as the antipruritic effective component) 25%

Comparison Result:

| | |
|---|---|
| Product of this invention | 60% |
| Commercially available product | 0 |
| Unable to evaulate | 40% |

EXAMPLE 1

To a proper amount of toluene were added 8.8 g of polybutene, 47.5 g of a petroleum resin (Quintons ® U-185, trade name, made by Nihon Zeon K. K.), and 31.7 g of a styrene-isoprene-isoprene copolymer resin (Cariflex ® TR-1107, trade name, made by Shell Kagaku Co., Ltd.) and they were dissolved therein under heating and after cooling, a solution of 2.0 g of glycyrrhetinic acid and 2.0 g of diphenhydramine dissolved in 8.0 g of benzyl alcohol was uniformly mixed with the above solution. The mixture was coated on a releasable liner and after evaporating off toluene, a polyvinyl chloride film was applied thereto.

EXAMPLES 2 TO 7

The following plasters were prepared according to the manner in Examples 1.

EXAMPLE 2

| | |
|---|---|
| Glycyrrhizic acid | 1.0 g |
| Chlorpheniramine | 1.0 g |
| N—Methyl-2-pyrrolidone | 9.0 g |
| SIS* (Cariflex ® TR-1107) | 32.0 h |
| Petroleum resin (Quintons ® TR-1107) | 48.1 g |
| Polybutene | 8.9 g |
| Total | 100.0 g |
| Solvent: toluene | proper amount |

EXAMPLE 3

| | |
|---|---|
| Stearyl glycyrrhetinate | 0.5 g |
| Diphenhydramine salicylate | 0.5 g |
| Crotamiton | 9.0 g |
| SIS* (Cariflex ® TR-1107) | 32.4 g |
| Petroleum resin (Quintons ®) U-185) | 48.6 g |
| Polybutene | 9.0 g |
| Total | 100.0 g |
| Solvent: toluene | proper amount |

EXAMPLE 4

| | |
|---|---|
| Dipotassium glycyrrhizinate | 0.5 g |
| Crotamiton | 10.0 g |
| Propylene glycol | 2.5 g |
| SIS* (Cariflex ® TR-1107) | 31.3 g |
| Petroleum resin (Quintons ® | |

-continued

| | |
|---|---|
| U-185) | 47.0 g |
| Polybutene | 8.7 g |
| Total | 100.0 g |
| Solvent: toluene | proper amount |

EXAMPLE 5

| | |
|---|---|
| Glycyrrhetinic acid | 1.0 g |
| Crotamiton | 5.0 g |
| Diphenhydramine | 1.0 g |
| Lauric acid diethanolamide | 5.0 g |
| SIS* (Cariflex ® TR-1107) | 29.9 g |
| Petroleum resin (Quintons ® U-185) | 49.3 g |
| Polybutene | 8.8 g |
| Total | 100.0 g |
| Solvent: toluene | proper amount |

EXAMPLE 6

| | |
|---|---|
| Glycyrrhetinic acid | 1.0 g |
| Diphenhydramine hydrochloride | 0.5 g |
| N—Methyl-2-pyrrolidone | 6.0 g |
| Diethylene glycol monoethyl ether | 4.0 g |
| SIS* (Cariflex ® TR-1107) | 30.1 g |
| Peteroleum resin (Quintons ® U-185) | 49.6 g |
| Polybutene | 8.7 g |
| Total | 99.9 g |
| Solvent: toluene | proper amount |

EXAMPLE 7

| | |
|---|---|
| Glycyrrhizic acid | 0.5 g |
| Crotamiton | 5.0 g |
| Chlorpheniramine maleate | 0.5 g |
| Benzyl alcohol | 5.0 g |
| SIS* (Cariflex ® TR-1107) | 35.2 g |
| Peteroleum resin (Quintons ® U-185) | 44.8 g |
| Polybutene | 9.0 g |
| Total | 100.0 g |
| Solvent: toluene | proper amount |

*In the above examples, SIS means a styrene-isoprene-styrene tereblock copolymer resin, made by Shell Kagaku Co., Ltd.

EXAMPLE 8

In 15.0 g of crotamiton were dissolved 1.5 g of glycyrrhizic acid and 0.1 g of an antioxidant, butylated hydroxytoluene (BHT) and after uniformly mixing the solution with 151.6 g of an acrylic resin emulsion (Primal® N-580-S, trade name, made by Acryl Chemical Co., Ltd., solid component 54.5–55.5%), the mixture was coated on a releasable liner followed by drying. Thereafter, a polyvinyl chloride film was applied thereto.

EXAMPLES 9 AND 10

Following plasters were prepared according to the manner shown in Example 8.

EXAMPLE 9

| | |
|---|---|
| Glycyrrhetinic acid | 1.0 g |
| Crotamiton | 6.0 g |
| Chlorpheniramine | 1.0 g |
| Isopropylmethylphenol | 1.0 g |
| BHT | 0.1 g |
| Acrylic resin emulsion (Primal ® N—580-S) | 165.2 g |
| Total | 174.3 g |
| | (100.0 g as solid component) |

EXAMPLE 10

| | |
|---|---|
| Glycyrrhetinic acid | 0.5 g |
| Crotamiton | 10.0 g |
| Diphenhydramine | 1.0 g |
| BHT | 0.1 g |
| Acrylic resin emulsion (Primal ® N-580-S) | 160.6 g |
| Total | 172.2 g |
| | (99.9 g as solid component) |

EXAMPLE 11

A mixture of 18.8 g of polybutene, 35.2 g of a petroleum resin (Quintons ® U-185, trade name, made by Nihon Zeon K. K.) and 4.9 g of liquid paraffin was heated to 100° to 120° C. to form a solution and after allowing to cool the solution to an inside temperature of 50°–60° C., the solution was uniformly mixed with a solution of 1.0 g glycyrrhizic acid and 0.1 g of BHT dissolved in 5.0 g of N-methyl-2-pyrrolidone. The mixture thus formed was further uniformly mixed with 25.5 g (60% solid component) of a styrene-butadiene copolymer latex and 19.5 g (60% solid component) of a natural rubber latex, the resultant mixture was coated on a releasable liner followed by drying, a polyvinyl chloride film was applied thereto.

EXAMPLES 12 TO 16

Following palsters were prepared according to the manner described in Example 11.

EXAMPLE 12

| | |
|---|---|
| Glycyrrhizic acid | 0.5 g |
| Diphenhydramine | 2.0 g |
| Lauric acid diethanolamide | 2.0 g |
| BHT | 0.1 g |
| Petroleum resin (Quintons ® U-185) | 32.5 g |
| Polybutene | 20.0 g |
| Liquid paraffin | 4.9 g |
| Styrene-butadiene copolymer latex | 23.2 g |
| | (60% solid component) |
| Natural rubber latex | 14.8 g |
| | (60% solid component) |
| Total | 100.0 g |
| | (84.8 g as solid component) |

EXAMPLE 13

| | |
|---|---|
| Glycyrrhetinic acid | 1.0 g |
| Diphenhydramine | 1.0 g |
| Crotamiton | 6.0 g |
| Isopropylmethylphenol | 1.0 g |
| BHT | 0.1 g |
| Petroleum resin (Quintons ® U-185) | 40.3 g |
| Polybutene | 15.7 g |
| Liquid paraffin | 4.9 g |

| | |
|---|---|
| Glycyrrhetinic acid | 1.0 g |
| Crotamiton | 6.0 g |

-continued

| | |
|---|---|
| Styrene butadiene copolymer latex | 29.0 g |
| | (60% solid component) |
| Natural rubber latex | 21.0 g |
| | (60% solid component) |
| Total | 120.0 g |
| | (100.0 g as solid component) |

EXAMPLE 14

| | |
|---|---|
| Glycyrrhetinic acid | 1.0 g |
| Diphenhydramine | 2.0 g |
| Isopropylmethylphenol | 0.5 g |
| N—Methyl-2-pyrrolidone | 2.0 g |
| Diethylene glycol monoethyl ether | 2.0 g |
| BHT | 0.1 g |
| Petroleum resin (Quintons ® U-185) | 35.2 g |
| Polybutene | 17.3 g |
| Liquid paraffin | 4.9 g |
| Styrene-butadiene copolymer latex | 26.0 g |
| | (60% solid component) |
| Natural rubber latex | 19.0 |
| | (60% solid component) |
| Total | 110.0 g |
| | (92.0 g solid as component) |

EXAMPLE 15

| | |
|---|---|
| Glycyrrhetinic acid | 0.5 g |
| Diphenhidramine | 2.0 g |
| Isopropylmethylphenol | 0.5 g |
| Isopropyl milistate | 4.0 g |
| BHT | 0.1 g |
| Petroleum resin (Quintons ® U-185) | 34.0 g |
| Styrene-butadiene copolymer latex | 23.7 g |
| | (60% solid component) |
| Natural rubber latex | 16.3 g |
| | (60% solid component) |
| Total | 100.0 g |
| | (87.0 g as solid component) |

What is claimed is:

1. An antipruritic plaster comprising a backing having formed on one surface thereof a pressure-sensitive adhesive layer containing:
   (1) from about 0.1 to about 10 percent by weight, based on the total weight of said plaster, of a glycyrrhetinic acid compound selected from the group consisting of glycyrrhetinic acid, glycyrrhizin and salts of glycyrrhizin,
   (2) from about 1 to about 20 percent by weight of at leastone solvent for dissolving said glycyrrhetinic acid compound selected from benzyl alcohol, phenethyl alcohol, diphenhydramine, chlorpheniramine and crotamiton, and
   (3) a base of either:
      (a) from about 75 to about 98.5 percent by weight based on the total weight of said adhesive layer of at least one rubber compound adhesive plaster base selected from natural rubber, a styrene-butadiene copolyer elastomer, and a styrene-isoprene-styrene copolymer elastomer; at least one tackifying agent selected from a petroleum resin, rosin, hydrogenated rosin, and an ester gum; and at least one softener selected from polybutene, liquid paraffin, a higher fatty acid ester, a silicon oil, and a vegetable oil, or
      (b) from about 65 to about 98.5 weight percent based on the total weight of said adhesive layer of an acrylic resin.
2. The antipruritic plaster claimed in claim 1, wherein the amount of component (1) is 0.2 to 4% by weight, the amount of component (2) is 5 to 15% by weight, and component (3)(b) is used as a base and the amount of the component is 70 to 97% by weight to the total amount of the medicament-containing adhesive mass, respectively.
3. The antipruritic plaster claimed in claim 1, wherein the glycyrrhetinic acids is glycyrrhetinic acid, the solvent for said glycyrrhetinic acid compound is selected from diphenhydramine and crotamiton, and the base is an acrylic resin.
4. A plaster of claim 3 further containing an antibacterial agent.
5. A plaster of claim 3 further containing an antioxident.
6. A plaster of claim 3 further containing a perfume.

* * * * *